United States Patent
Mejlhede et al.

(10) Patent No.: US 9,211,379 B2
(45) Date of Patent: Dec. 15, 2015

(54) INSERTER FOR INFUSION PART AND INFUSION PART PROVIDED WITH NEEDLE PROTECTOR

(75) Inventors: Signe T. Mejlhede, Svinninge (DK); Lasse W. Mogensen, Søborg (DK); Magnus W. Göransson, Malmö (SE)

(73) Assignee: UNOMEDICAL A/S, Birkerød (DK)

( * ) Notice: Subject to any disclaimer, the term of this patent is extended or adjusted under 35 U.S.C. 154(b) by 1163 days.

(21) Appl. No.: 12/280,867

(22) PCT Filed: Feb. 28, 2007

(86) PCT No.: PCT/DK2007/050026
§ 371 (c)(1),
(2), (4) Date: Jun. 23, 2009

(87) PCT Pub. No.: WO2007/098771
PCT Pub. Date: Sep. 7, 2007

(65) Prior Publication Data
US 2010/0022960 A1    Jan. 28, 2010

Related U.S. Application Data

(60) Provisional application No. 60/778,086, filed on Feb. 28, 2006.

(30) Foreign Application Priority Data

Feb. 28, 2006   (DK) .................................. 2006 00282

(51) Int. Cl.
*A61M 5/178*   (2006.01)
*A61M 5/158*   (2006.01)
*A61M 25/06*   (2006.01)

(52) U.S. Cl.
CPC ........... *A61M 5/158* (2013.01); *A61M 25/0612* (2013.01); *A61M 2005/1585* (2013.01); *A61M 2005/1587* (2013.01)

(58) Field of Classification Search
CPC ..................... A61M 5/158; A61M 2005/1585; A61M 25/0631; A61M 25/0612; A61M 2005/14252; A61M 25/0606
USPC ................ 604/164.08, 263, 164.12, 192, 198
See application file for complete search history.

(56) References Cited

U.S. PATENT DOCUMENTS 1,592,462 A   7/1926   MacGregor
2,047,010 A   7/1936   Dickinson
(Continued)

FOREIGN PATENT DOCUMENTS

DE   4 342 329 A1   6/1994
DE   196 31 921 A1   3/1997
(Continued)

OTHER PUBLICATIONS

International-Type Search Report for Danish Application No. DK 200600282 completed Oct. 12, 2006.
(Continued)

*Primary Examiner* — Emily Schmidt
(74) *Attorney, Agent, or Firm* — Wilson, Sonsini, Goodrich & Rosati

(57) ABSTRACT

The invention relates to an infusion part (1), as well as to a simple, non-expensive inserter for said infusion part which inserter would be easy and safe for the user to handle during use and to dispose of after use. The inserter comprises a housing (26), a spring unit (19) and a sled unit (11) connected to the housing via the spring unit. The infusion part comprises a cannula (6) integrated with an insertion needle (7) and a needle protection (4) releasably secured to the infusion part and removable from the position where it protects the needle by applying a force perpendicular to the axis of the needle.

8 Claims, 6 Drawing Sheets

(56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teissen-Simony |
| 5,527,287 A | 6/1996 | Miskinyar et al. |

(56) References Cited

U.S. PATENT DOCUMENTS

| | | |
|---|---|---|
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |

(56) References Cited

U.S. PATENT DOCUMENTS

| | | |
|---|---|---|
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkinson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 | 12/2012 | Chong et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Pluth et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |

(56) References Cited

U.S. PATENT DOCUMENTS

| | | |
|---|---|---|
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheider et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0058692 A1 | 3/2008 | Propp et al. |
| 2008/0200897 A1 | 8/2008 | Hoss et al. |
| 2008/0269687 A1 | 10/2008 | Chong |
| 2008/0312601 A1 | 12/2008 | Cane |
| 2009/0062767 A1 | 3/2009 | Van Antwerp et al. |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1 | 9/2010 | Nielsen |
| 2010/0262078 A1 | 10/2010 | Blomquist |
| 2011/0054399 A1 | 3/2011 | Chong et al. |

FOREIGN PATENT DOCUMENTS

| | | |
|---|---|---|
| DE | 299 05 071 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0 688 232 A1 | 9/1994 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0714631 B1 | 6/1996 |
| EP | 0744183 A2 | 11/1996 |
| EP | 0747006 A1 | 12/1996 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 1329233 A1 | 7/2003 |
| EP | 1 350 537 A1 | 10/2003 |
| EP | 1360970 A1 | 11/2003 |
| EP | 1380315 A1 | 1/2004 |
| EP | 1 407 793 A1 | 4/2004 |
| EP | 1407747 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |

(56) References Cited

FOREIGN PATENT DOCUMENTS

| | | |
|---|---|---|
| EP | 1776980 A1 | 4/2007 |
| EP | 1970091 A1 | 9/2008 |
| EP | 2272559 A1 | 1/2011 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/068014 A3 | 1/2003 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A1 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A1 | 8/2008 |
| WO | WO 2008/092959 A1 | 8/2008 |
| WO | WO 2008/133702 A1 | 11/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |

(56) References Cited

FOREIGN PATENT DOCUMENTS

| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |

OTHER PUBLICATIONS

International Search Report for International Application No. PCT/DK2007/050026 completed Aug. 23, 2007.

International Preliminary Report on Patentability for for International Application No. PCT/DK2007/050026 completed Jun. 11, 2008.

"Why inset®?" inset® infusion set product overview; http://web.archive.org/web/20040906102448/http://www.infusion-set.com/Default.asp?ID=108; two pages.

INSERTER FOR INFUSION PART AND INFUSION PART PROVIDED WITH NEEDLE PROTECTOR

This application claims the benefit under 35 U.S.C. §371 of International Application No. PCT/DK2007/050026, filed Feb. 28, 2007, which claims the benefit of Danish Patent Application No. PA 2006 00282, filed Feb. 28, 2006, and U.S. Provisional Application Ser. No. 60/778,086, filed Feb. 28, 2006. These references are incorporated herein in their entirety.

TECHNICAL FIELD

The invention relates to an inserter for an infusion part comprising a needle protector and an infusion part comprising a needle protector which infusion part is used for intermittent or continuous administration of a therapeutical substance, such as e.g. insulin. The infusion part comprises a cannula integrated with an insertion needle.

BACKGROUND OF THE INVENTION

Traditionally needle protectors for insertion needles of infusion parts are either part of the disposable packing of the inserter part or the needle protector is fastened to the infusion part and pulled away from the infusion part in direction of the insertion needle.

If the needle protector is a part of the packing in which the infusion part is delivered to the user, then the user will have to remove the packing including the needle protector some time before the infusion part is inserted, and the user will definitely have to remove the packing before the inserter or the infusion part is positioned at the skin of the user. This means that the insertion needle will be exposed for a relatively long time if the packing forms the needle protector.

If the needle protector is fastened directly to the infusion part when the infusion part is combined to a needle hub or to an automatic inserter, then the infusion part and the needle protector is normally placed on a line where first the needle protector is pulled of the insertion needle, then the infusion part is inserted and at last the device comprising a separate insertion needle is removed from the infusion part while the infusion part stay positioned subcutaneously. As all three components are to be removed along the axis formed by the insertion needle there is a risk that the needle hub/inserter is separated from the infusion part as the needle protector is removed from the infusion part. The user might need to compensate from this risk by holding the infusion part back with a finger while removing the needle protector.

The present invention is equally well-suited for all kind of infusion parts whether it is a low-profile, angled infusion part or it is an infusion part having the insertion needle positioned perpendicular to the proximal surface of the infusion part.

In this document the expression "infusion set" is used to describe the combination of a connector part, a needle hub or an inserter combined with an infusion part.

DESCRIPTION OF INVENTION

The object of the invention is to provide a needle protector and an infusion part comprising this needle protector which needle protector protects the user from touching an insertion needle right up to the time of insertion and which needle protector at the same time is easy to remove from the protective position without the user having to hold back parts with his fingers during removal.

Also it is an object of the invention to provide a simple, non-expensive inserter for an infusion part which inserter would be easy and safe for the user to handle during use and to dispose of after use.

The invention concerns a needle protector protecting an insertion needle of an infusion part which needle protector comprises at least one side part covering the side of the insertion needle wherein the side part is provided with an opening in order for the insertion needle to pass through the side of the needle protector when the needle protector is moved to a position which allows for insertion of the insertion needle before use.

When the needle protector is removed by a movement mainly perpendicular—or at least not parallel—to the direction of the insertion needle no forces parallel to the direction of the insertion needle will appear. That the movement should be mainly perpendicular means that the component of the force applied to the needle protector should have a perpendicular component (perpendicular to the insertion needle) which is larger than the parallel component (parallel and pointing in the same direction as the insertion needle) of the applied force.

This reduces the risk of pulling the infusion part away from an inserter device or e.g. a needle hub in which the infusion part is positioned. In one embodiment the needle protector can be secured to the infusion part in one or more tracks or recesses in the surface of the infusion part which tracks or recesses would be in the form of one or more lines leading from the protective position to the border of the infusion part making it possible to push the needle protector away from the infusion part in a side way movement. Preferably any component of force in direction of the axle formed by the insertion needle and away from the infusion part should be avoided completely.

According to a preferred embodiment of the invention the needle protector is removed from the infusion part by turning the needle protector around a point or an axle close to the surface of the infusion part.

According to this embodiment the force applied to the needle protector will at first be perpendicular to the direction of the insertion needle and after that point in direction of the surface of the infusion part. When the needle protector is removed by a turning movement and the needle protector touches the infusion part at two points at least in the direction of the turning movement, then a part of the needle protector will be pushed toward the infusion part when the needle protector is turned away in order to prepare the infusion part for use.

According to another embodiment the needle protector is directly or indirectly secured to a mounting pad. That the needle protector is directly secured to the mounting pad means that surface contact between needle protector and mounting pad exists. That the needle protector is indirectly secured to the mounting pad means that there is no direct surface contact between the two units e.g. the needle protector could be connected to the release paper.

The invention also concerns an infusion part comprising a cannula integrated with an insertion needle, and a needle protector releasably secured to the infusion part wherein the needle protector is removed from one position where it protects the insertion needle by applying a force in a direction perpendicular to the axis formed by the insertion needle or in a direction toward the infusion part. That the cannula is integrated with the insertion needle means that the cannula and the insertion needle are so closely adjoined that the cannula and the insertion needle can be inserted together, normally by placing the dimensionally stable insertion needle inside the hollow soft cannula, but they can also be integrated by providing an insertion needle with cannula functions i.e. the insertion needle is hollow and stays inserted into the patient functioning as a cannula.

According to a preferred embodiment the infusion part comprises at least one mounting pad and the needle protector is releasably secured to the mounting pad. Preferably the mounting pad is secured unreleasably to the infusion part.

According to another preferred embodiment the needle protector—totally or partly—is constructed of a material which cannot be penetrated by the insertion needle.

In yet a preferred embodiment the mounting pad has a proximal side at least partly provided with adhesive. The proximal side of the mounting pad is the side turned toward the patient during use.

According to a preferred embodiment the needle protector is directly or indirectly secured to a surface of the mounting pad which is at least partly provided with adhesive. Preferably the needle protector is integrated with a release layer and the release layer is adhered to the proximal side of the mounting pad. That the needle protector is integrated with means that it is either secured to or forms a part of the release layer contact surface.

According to another preferred embodiment the needle protector is provided with an adhesive surface.

The invention also concerns an inserter comprising a housing, a spring unit, and a sled unit which sled unit is releasably connected to an infusion part, the sled unit is connected to the housing via the spring unit and can be moved from at least a first position to at least one second position relative to the housing, the infusion part comprises a cannula integrated with an insertion needle wherein a needle protector is releasably connected to the infusion part. According to the invention the needle protector is connected to the infusion part where "connected to the infusion part" means that the needle protector is connected to a part which part together with other parts constitutes the infusion part. In one embodiment the infusion part is provided with at least one mounting pad and the needle protector is releasably connected to the mounting pad.

In a most preferred embodiment the needle protector interacts with a part of the housing and one way to let the needle protector interact with the housing is to have the needle protector made of a dimensionally stable material which is fastened to the infusion part in at least two positions.

According to this preferred embodiment of the invention the sled unit when brought from one position to a second position will cause a first contact surface of the needle protector to contact a surface integrated with the housing to stop the movement of the first contact surface, at the same time the second contact surface of the needle protector will continuously move toward the second position. The different velocities of the needle protector at different positions will change the angle of the needle protector relative to the direction of movement The invention also concerns an inserter comprising a housing, a spring unit, and a sled unit which sled unit is releasably connected to an infusion part and can be moved from at least a first position to at least one second position relative to the housing, the infusion part comprises a cannula integrated with an insertion needle wherein the sled unit is connected to the housing via the spring unit. In a preferred embodiment the spring unit is shaped as a ring having two spring functioning parts. That the sled unit is connected to the housing via the spring unit means that the sled unit has no direct contact with the housing which makes it possible to produce a standard housing and combined it with varying spring units adapted to a desired sled unit.

In a preferred embodiment of this inserter according to the invention a first connecting part connecting two ends of the two spring functioning parts are fastened the sled unit and a second connecting part connecting the other two ends of the spring functioning parts are fastened to the housing. In a more preferred embodiment the second connecting part connecting the other two ends of the spring functioning parts is connected to the top back of the housing.

In another preferred embodiment the second connecting part is formed with protruding fastening means which both connects the spring unit to the housing and provides guiding means for the sled unit.

The invention concerns a disposable, low-profile inserter for an angled infusion set which inserter comprises a set housing, a cannula housing, a needle hub, a spring unit and a carrier body, where
  the set housing is provided with guiding means on the internal surface for securing the movement of the carrier body,
  the cannula housing comprises a soft cannula to be placed subcutaneously,
  the needle hub comprises a needle for piercing of the skin,
  the cannula housing and the needle hub are releasably fastened to each other and when fastened to each other the needle is adjoined the cannula; preferably the needle is placed inside the cannula;
  the carrier body is provided with guiding means on the external surface which secures the movement relative to the set housing (1) from a retracted to an advanced position,
  the carrier body is connected to release means, and when the release means are manipulated, the carrier body, the cannula housing and the needle hub are forced by the spring unit to an advanced position where the needle and cannula will be placed subcutaneous when the user holds the device against the skin,
  the needle hub and the carrier body are provided with unreleasable interacting locking means.

"Adjoined" means that the needle is placed adequately close to the cannula to assure the subcutaneously insertion of the cannula whether the needle is placed inside, beside or around the cannula.

According to one embodiment of the invention the needle hub and the carrier body are created as a single unit e.g. by molding together a movable part of the set housing and a needle hub or e.g. by fastening an insertion needle directly to a movable part of the set housing. According to the present invention it is also possible to use an infusion set known per se as for example the set known from EP 688232 B1 forming an unreleasable connection between a carrier body and the needle hub where after the needle unit comprising the carrier body and the needle hub are fastened in the set housing during production of the inserter. The unreleasable connection could be formed e.g. by gluing, welding or by mechanically locking the two units to each other.

In a preferred embodiment the unreleasable connection between the carrier body and the needle hub is formed by making openings in a part of the needle hub which is covered by a solid part of the set housing, and by making corresponding projections in the carrier body. When the set housing is placed around the needle unit ("around" meaning that material of the set housing covers the needle unit on at least two opposite sides) either the elasticity of the set housing will squeeze the two opposite sides together and thereby squeeze the needle hub and the carrier body together, or the confined space created by two opposite sides of an essentially rigid set housing will force the projections of the carrier body and the openings of the needle hub together and form an unreleasable connection between the carrier body and the needle hub as the openings of the needle hub and the projections of the carrier body fit perfectly together.

According to another embodiment of the invention the needle unit is locked to the inserter after use. When the needle unit is locked to the inserter after use it will be possible for the user to remove both the inserter and the needle unit by only grabbing the inserter, instead of the user holding on to both inserter and needle unit after use. According to the embodiment shown in FIGS. 1-3 the needle unit is locked to the inserter because the needle unit can only move in a confined space. The confined space is limited by the U-shaped set housing on three sides, by the guiding means of the set housing and the needle unit on two sides as the guiding means prevents sideways movements and by the stopper 12 which prevents the needle unit from moving forward beyond a fixed point.

According to another embodiment of the invention it is possible to move the needle unit back from the advanced position where the needle can pierce the skin of a patient to a retracted position in order to diminish the risks of getting into contact with the used needle.

According to another embodiment of the invention the lower part of the set housing—where the lower part of the set housing is the side closest to the user during insertion—could be prolonged and turned upward in relation to the base line (the base line is a line parallel to the needle but at a lower level where a "lower level" means a level closer to the user, normally the level provided by the lower side of the set housing). This prolongation or projection of the lower part provides an appropriate contact between the skin of the patient and the inserter in order to have the cannula inserted in a proper angle, and also the prolonged or projecting part lifts up the mounting pad to a proper position for contact with the skin.

The end of the projecting part should preferably pass beyond the line formed by the needle/cannula in front of the end of the insertion needle when the needle unit is in a retracted position. This makes it necessary to provide an opening in the prolongation in order for the needle/cannula to be able to pass through. According to the embodiment of FIGS. 1-3 this is obtained by separating the projecting part into two legs. In this embodiment the projecting part is formed as a mathematical continuous curvature but it could also be non-continuous, i.e. being provided with one or more breaks.

In another aspect of the invention the set housing is made out of a single piece of material. That the needle hub housing is constructed of one piece of material means that no screws or the like is needed to assemble or fasten the casing surrounding the carrier body and the inserter set. The set housing could be produced by molding, i.e. injection molding or by any other known technology. Also the set housing could be produced as e.g. two halves which afterwards are glued or welded together. The set housing could be made of plastic or metal or any other suitable material having the necessary mechanical properties.

The inserter according to the invention is of a simple construction and consists of relatively few parts and thus it will be less expensive to produce and assemble. This renders the inserter especially suitable for use as a disposable product.

In yet another embodiment the set housing is formed of a single U-shaped piece of material. The set housing is U-shaped which means that it is constructed of a rectangular or elliptic piece of flat material which is bent in such a way that the ends of the material—seen from the side—forms two substantial parallel legs connected in one end with a straight or arched line, where the legs are not necessarily of the same length. The material is of a bend form which does not mean that it is constructed by bending; it could e.g. be molded in a bend form. When the set housing is U-shaped the part called the lower leg is the leg in contact with the user when the inserter is in position for insertion of the infusion part.

In another embodiment the set housing is formed as a piece of pipe with a rounded or poly-sided cut-through profile.

In yet another embodiment the spring unit is fastened to the set housing in a first position and to the carrier body or the needle unit in a second position, where the first position is situated closer to the front end of the set housing than the second position when the spring unit is biased, where the front end of the set housing is the end of the set housing nearest the user during insertion. This feature will result in that the carrier body and the needle hub together form a single unit which is pulled forward relative to the housing when the release means are activated. The spring unit could be made of any material which retracts to a relaxed unbiased position, preferably made of rubber, plastic or metal.

DESCRIPTION OF THE DRAWINGS

The invention is explained in greater detail below with reference to the accompanying drawings wherein a preferred embodiment of the invention is shown.

FIG. 1 shows an infusion set with an infusion part according to the invention. The infusion set comprises an infusion part 1, a needle hub 3, a mounting pad 2, a needle protector 4 and a release layer 5 protecting an adhesive layer of the mounting pad 2, the release layer 5 in this embodiment is provided with two handles, which makes it easier to remove the release layer 5, one on each side of the infusion part 1 extending in relation to the surface of the mounting pad 2. The infusion part 1 comprises means for connecting the infusion part 1 releasably to the needle hub 3 and it comprises a cannula 6. An insertion needle 7 has to be integrated with the cannula in order to make it possible to penetrate the skin of the user and position the cannula 6 subcutaneous and in this embodiment the insertion needle 7 extends from the needle hub 2 through the hollow center of the cannula 6. The insertion needle 7 can be placed inside the cannula 6, beside the cannula 6, around the cannula 6 and the cannula 6 can be made of a hard material which makes it possible for the cannula 6 to perform as insertion needle 7. When it in this application is said that the cannula 6 is integrated with the insertion needle 7 it could mean any of the aforementioned possibilities.

In FIG. 1 a needle protector 4 is releasably secured to the infusion part 1. That the needle protector 4 is releasably secured to the infusion part 1 means that it is possible to change the position of the needle protector 4 in order for the needle protector 4 in a first position to protect the insertion needle 7 and in a second position to allow for insertion of the cannula 6 integrated with the insertion needle 7.

FIG. 2 shows a preferred embodiment of a needle protector 4 according to the invention. The needle protector 4 comprises an infusion part contact surface 9, a protective surface 10 and a housing contact surface 8. The infusion part contact surface 9 is secured to the infusion part 1 either directly or indirectly. That the infusion part contact surface 9 is directly in contact with the infusion part 1 means that the infusion part contact surface 9 is in physical contact with the infusion part 1 and actually touches it. That the infusion part contact surface 9 is indirectly in contact with the infusion part 1 means that the surface 9 does not actually touch the infusion part 1 but is connected to a part secured to the infusion part 1 e.g. the mounting pad 2 which is the case in the embodiment of FIG. 1. The protective surface 10 covers two sides of the insertion needle 7 and the pointy tip, one side ("upwards" in FIG. 2) of the insertion needle 7 is protected by the lower side of the infusion part 1 and the opposite side ("downwards" in FIG. 2) is open and the insertion needle 7 can pass through this open side when the needle protector 4 is moved to a second position allowing for insertion of the cannula 6. In this embodiment the needle protector 4 is provided with a housing contact surface 8. This surface 8 is raised from the surface of the infusion part 1 to which the needle protector 4 is secured. The housing contact surface 8 is used as an axle when tipping the needle protector 4 from a first position to a second position; this shift from one position to another is explained more thoroughly in the description for FIGS. 7 and 8.

FIG. 3 shows an infusion set comprising an infusion part 1 and a needle hub 3 which set can be applied as part of the invention. The infusion set as such is known from the prior art. The two parts 1 and 3 can be releasably connected to each other, i.e. during insertion the needle hub 3 and the infusion part 1 are joined together and after insertion the needle hub 3 is released from the infusion part 1 and disposed of. In a preferred embodiment a needle hub 3 used for insertion is unreleasably connected to a disposable inserter. In such an embodiment the needle hub 3 is disposed of together with the inserter after use. The infusion part 1 comprises means 23 for connecting the infusion part 1 releasably to the needle hub 3 and the needle hub 3 comprises means 24 corresponding to the means of the infusion part 1. In this embodiment the means 23 of the infusion part 1 comprise to openings placed on opposite sides of the middle section of the infusion part 1. The middle section of the infusion part 1 comprises a through going opening forming a fluid connection through the infusion part 1 to the cannula 6. The middle section is provided with openings for a set of guiding means 25 of the needle hub 3. The guiding means 25 helps forming a stable connection between the needle hub 3 and the infusion part 1. The needle hub 3 comprises a set of arms 21 which is used when the needle hub 3 is released from the infusion part 1, in order to release the needle hub 3 from the infusion part 1 the two arms 21 are pushed together and toward the middle section of the infusion part 1. This movement releases the hooks of the means 24 for connecting of the needle hub 3 from the infusion part 1.

In the infusion part 1 of the present embodiment the cannula 6 extend in the same direction as the trough going opening but the cannula could just as well extend from the surface of the infusion part 1 perpendicular to this direction or in any other angel. Also an infusion part 1 used according to the present invention do not necessarily need to be able to connect to a needle hub 3 or a connector part 20, if the cannula 6 is made by a hard material and is able to penetrate the skin of the user without a separate insertion needle there is no need for a separate needle hub 3, and if the infusion part 1 has the form of an injection site through which drugs can be injected with a syringe there will be no need for a connector part 20.

Figure 1:
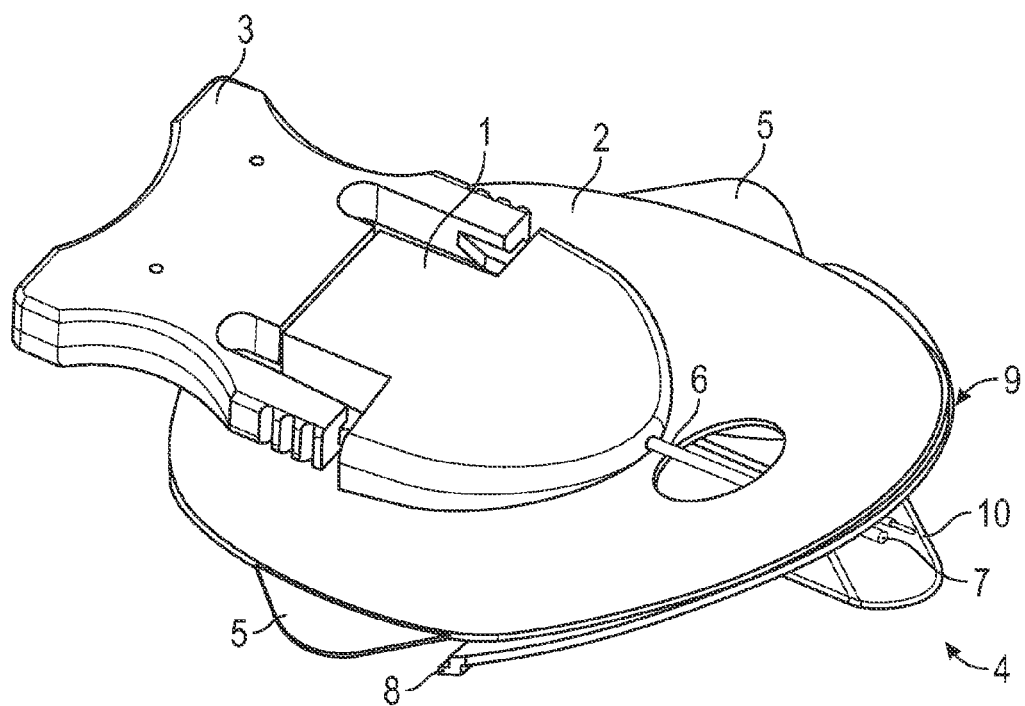
FIG. 1 shows an infusion part according to the invention.
Figure 2:
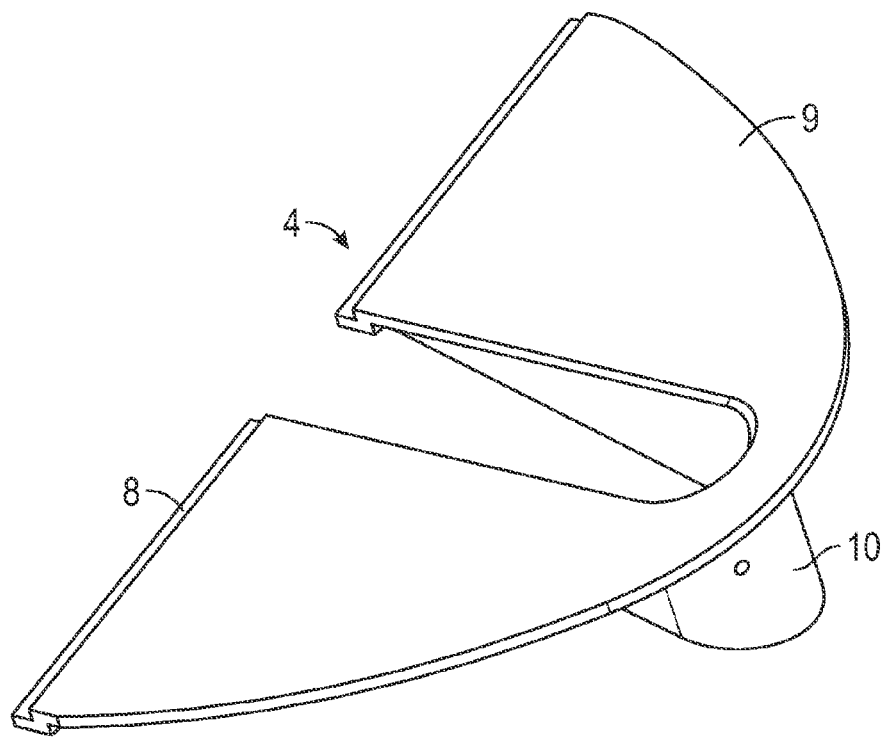
FIG. 2 shows a needle protector according to the invention.
Figure 3:
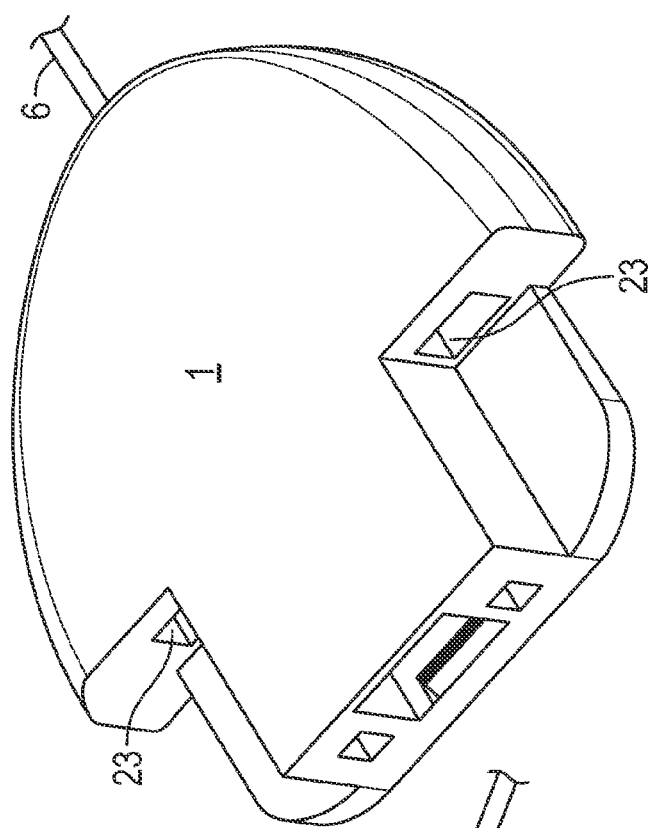
FIG. 3 shows an infusion set comprising an infusion part and a needle hub which set can be applied as part of the invention.
Figure 3:
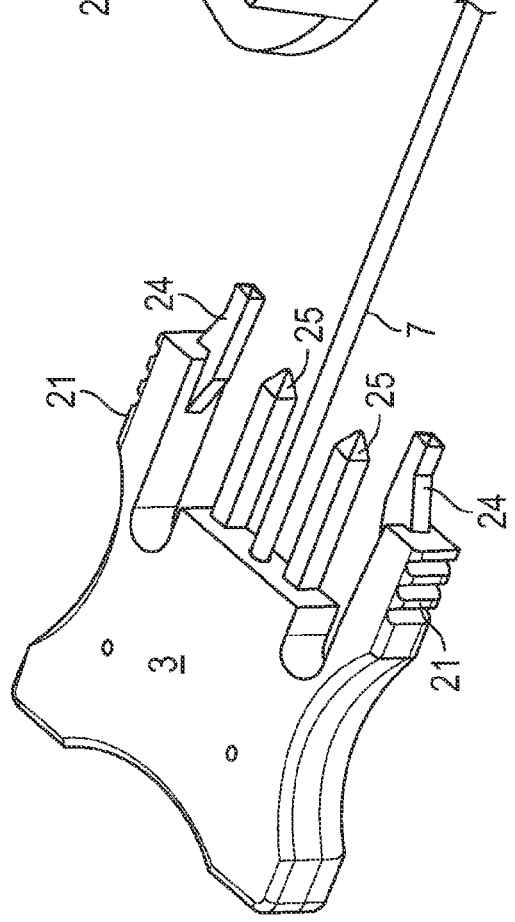
Figure 4:
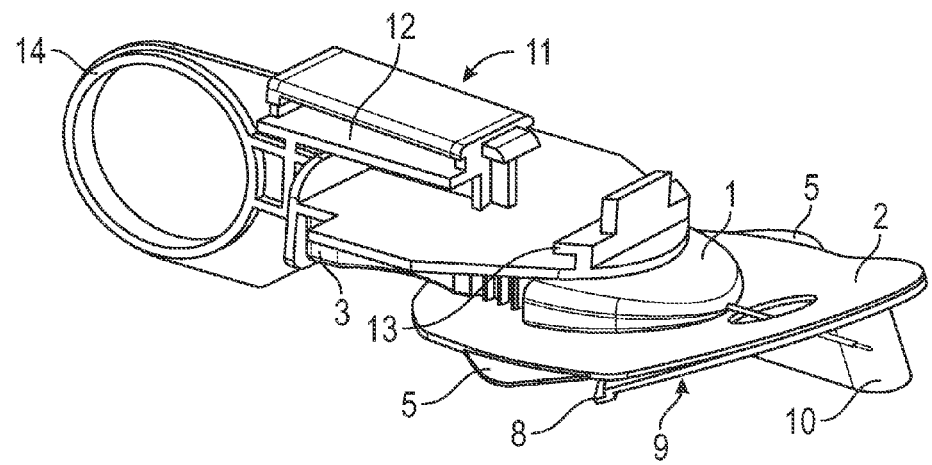
FIG. 4 shows an infusion set according to the invention combined with a sled.

FIG. 4 shows an infusion part 1 according to the invention combined with a sled 11 for positioning inside an automatic inserter. The sled 11 is provided with not shown means for securing the needle hub 3; the infusion part 1 is secured indirectly to the sled 11 via the needle hub 3. The sled further comprises guiding means 12, a handle 14 and means for fastening 13 a spring unit 19. The guiding means 12 assures that the sled 11 can travel inside an inserter along a well-defined path, the protruding edges formed by the guiding means 12 will slide from a forward to a retracted position in corresponding means formed in a non-movable part of the inserter or formed by one or more parts stationary in relation to the inserter. The handle 14 is in this embodiment positioned opposite the protruding cannula 6 of the infusion part 1. The handle 14 has a large opening which makes it easy to catch with a finger and to pull back. The means for fastening 13 of the spring unit 19 is positioned at the front end of the sled, and according to this embodiment of sled the spring unit 19 should push against the upright part of the fastening means 13 while the horizontal part of the fastening means 13 prevents the spring unit 19 from escaping pressure by sliding upwards.

Figure 5:
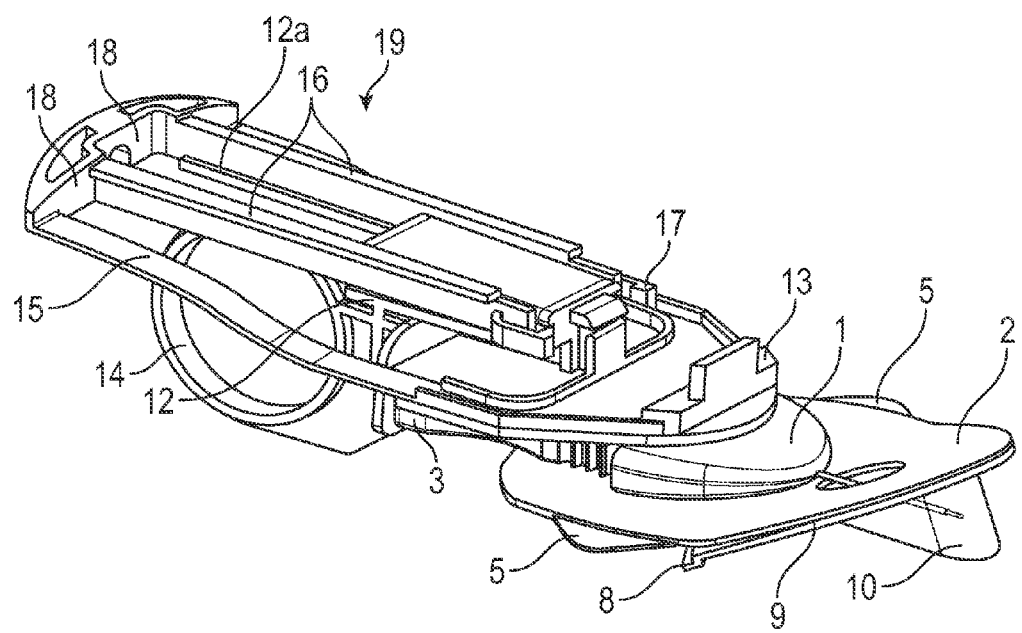
FIG. 5 shows an infusion set according to the invention combined with a sled and with a spring unit.

FIG. 5 shows an infusion part 1 according to the invention combined with a sled 11 and with a spring unit 19. The spring unit 19 is in this embodiment made of plastic and comprises a spring functioning part 15, secondary fastening means 16, stop parts 17 for secondary fastening means 16 and back stop 18 for the secondary fastening means 16. The spring functioning part 15 comprises two flat springs positioned on opposite sides of the sled 11, and the spring functioning parts 15 together with an end piece and a front piece forms a closed ring which makes it strong and easy to handle. When the spring functioning parts 15 are biased and the end piece and the front piece are brought together the spring functioning parts 15, which in FIG. 5 are shown in the unbiased form, are bend and form an S- or a C-like curve. In this embodiment the spring unit 19 is fastened to the housing 26 of the inserter by the secondary fastening means 16 which are positioned along the inside top wall of the inserter.

Compared to FIG. 4 the sled is now provided with the spring unit 19 which is fastened to the sled 11 with the fastening means 13. In order to position this embodiment of the spring unit 19 it is only necessary to force the front end of the spring unit 19 down between the raised middle part of the sled 11 and the fastening means 13.

Figure 6:
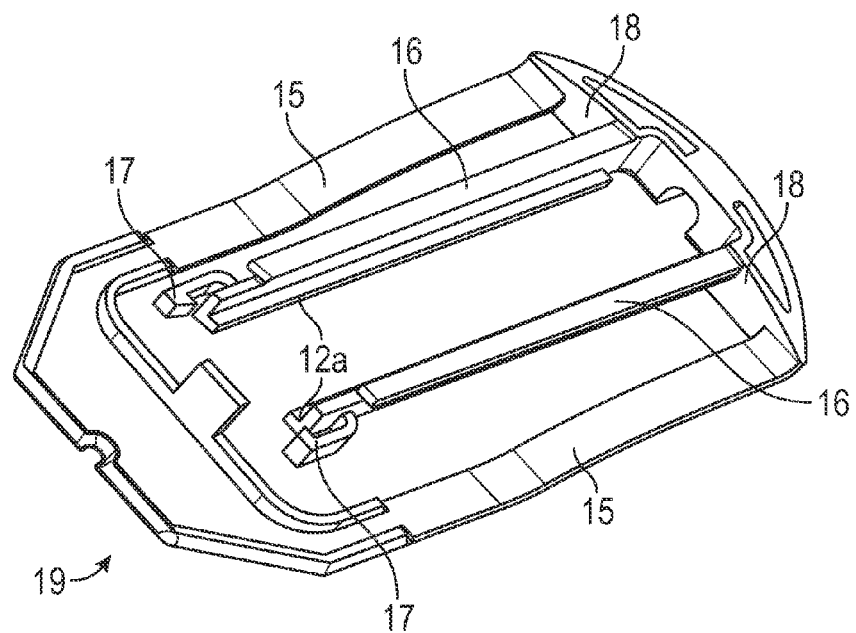
FIG. 6 shows a spring unit according to the invention.

FIG. 6 shows a spring unit 19 according to the invention.

Spring units of the type shown in FIG. 6 can e.g. be made of steel and in plastic. Spring units 19 in plastic would preferably be made of POM (Polyoxymethylene), and set housing, hard case top and carrier body would preferably be made of PP (Polypropylene).

If the spring unit and the carrier body in stead are molded together as one unit the preferred material would be POM. In this description the expression "flat spring" comprises "leaf spring".

In stead of using a spring unit 19 to bring the infusion part 1 from a retracted to a forward position it would be possible to use magnets. When using magnets repulsive magnets with an adequate repulsive force to move the infusion part 1 from a retracted to a forward position should be chosen. One magnet is placed in the housing 26 and another magnet is placed at the sled 11 carrying the infusion part 1. The repulsion between the magnets will force the infusion part 1 in a forward direction when releasing the sled 11 by activating a release button. The magnets can be molded into the housing 26 and into the sled 11 respectively in order to protect and hide the magnets. Further the repulsive magnets should be made in different sizes in order to avoid that the magnetic field changes.

Figure 7:
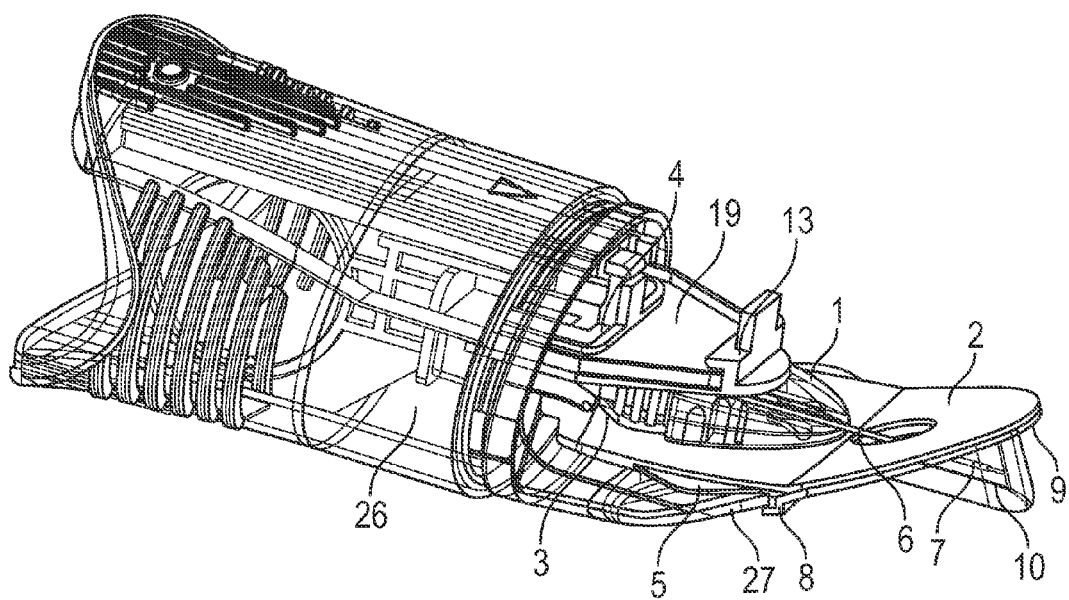
FIG. 7 shows an infusion set according to the invention combined with a sled and with a spring unit and placed in a housing.

FIG. 7 shows an infusion part 1 according to the invention combined with a sled 11 and a spring unit 19, all placed in an inserter with a housing 26. The inside of the inserter, which comprises the sled 11 combined with the infusion part 1, is in an unbiased position. The inside of the inserter would be brought into a biased position if the handle 14 is pulled back, when the handle is pulled far enough backwards a part of the inside will be positioned behind a stop which will prevent the inside of the inserter to return to a forward position before a release button has been activated. At the front end the housing 26 is provided with an upward bend part 27 which is used for positioning the inserter during insertion of the infusion part 1, before insertion the upward bend part 27 is according to this embodiment also used for positioning of the needle protector 4 and the mounting pad 2, this positioning assures that the mounting pad 2 has an adhesive surface directed towards the skin of the user when the infusion part 1 is inserted. The upward bend part 27 and the needle protector 4 are created in such a way that they correspond to each other and the protective surface of the needle protector 4 fits into an opening in the upward bend part 27.

Figure 8:
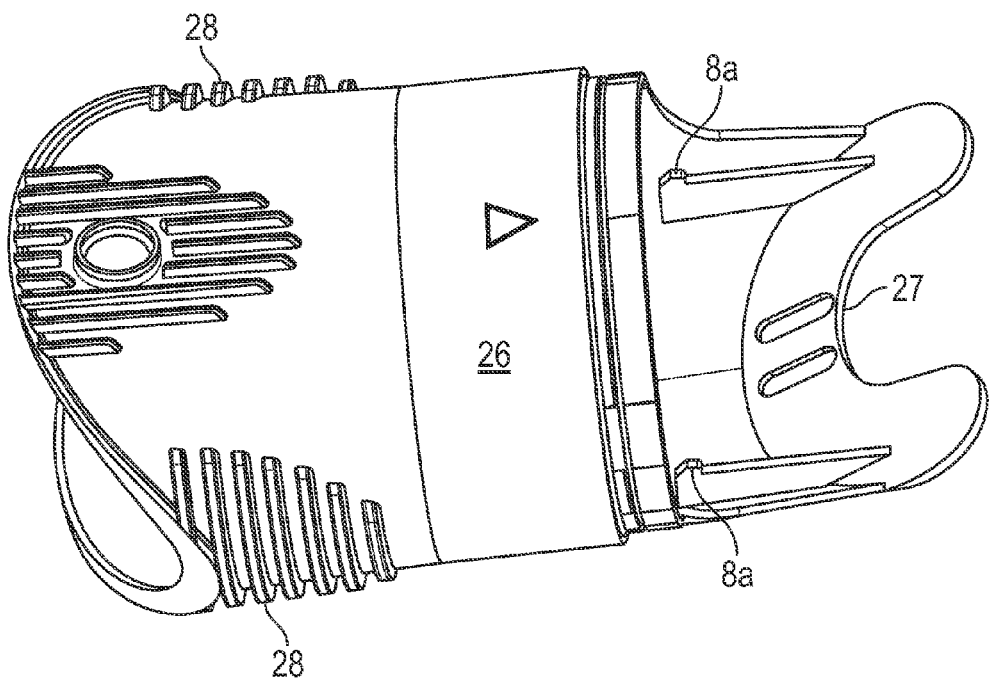
FIG. 8 shows a housing for an inserter according to the invention.

FIG. 8 shows a housing 26 for an inserter according to the invention. The housing 26 comprise an upward bend part 27 at the front end of the housing 26 and two pressure points 28 at the back end. Also the housing 26 comprise two protruding parts 8a which interact with the housing contact surface of the needle protector 4.

When the handle 14 of the sled 11 is pulled back, the needle protector 4 which is releasably connected to the infusion part 1 slides backward biasing the spring unit 19. When the housing contact surface 8 of the needle protector 4 touches the protruding parts 8a of the housing, the front end of the needle protector 4 is elevated as the front end of the needle protector 4 is connected to the infusion part 1 through the adherence to the mounting pad 2 and therefore continues to move backward while on the same time both the horizontal and the vertical position of the backend of the needle protector 4 at the housing contact surface 8 is stationary.

Figure 9:
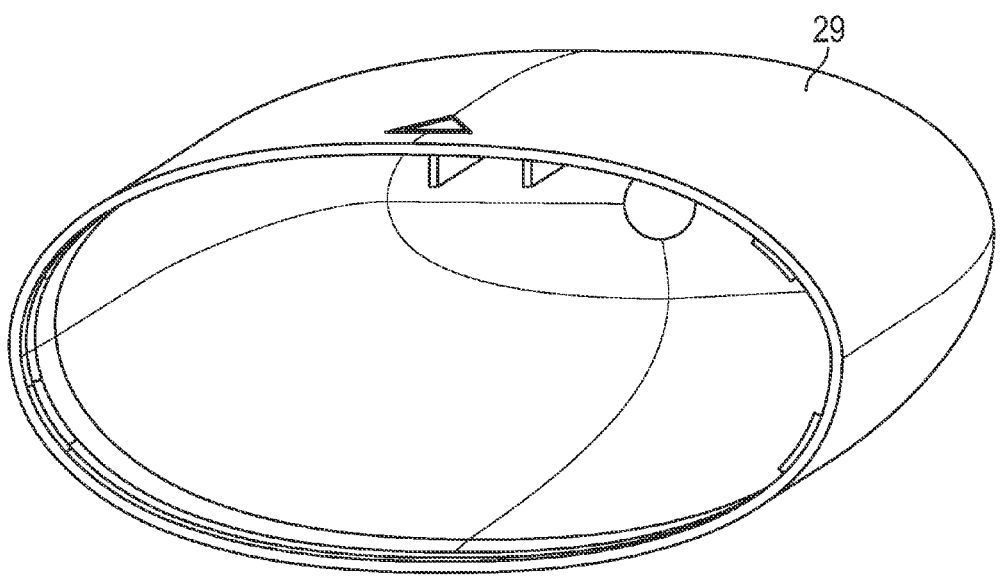
FIG. 9 shows a cover for a housing according to the invention.

FIG. 9 shows a cover 29 for the housing 26 of an inserter according to the invention. The cover 29 can be fastened to the housing 26 of the inserter before and after insertion. When it is fastened to the housing 26 before insertion it keeps the insertion part 1 and the inserter sterile and after insertion it can protect the surroundings from the potentially infectious insertion needle 7.

Figure 10:
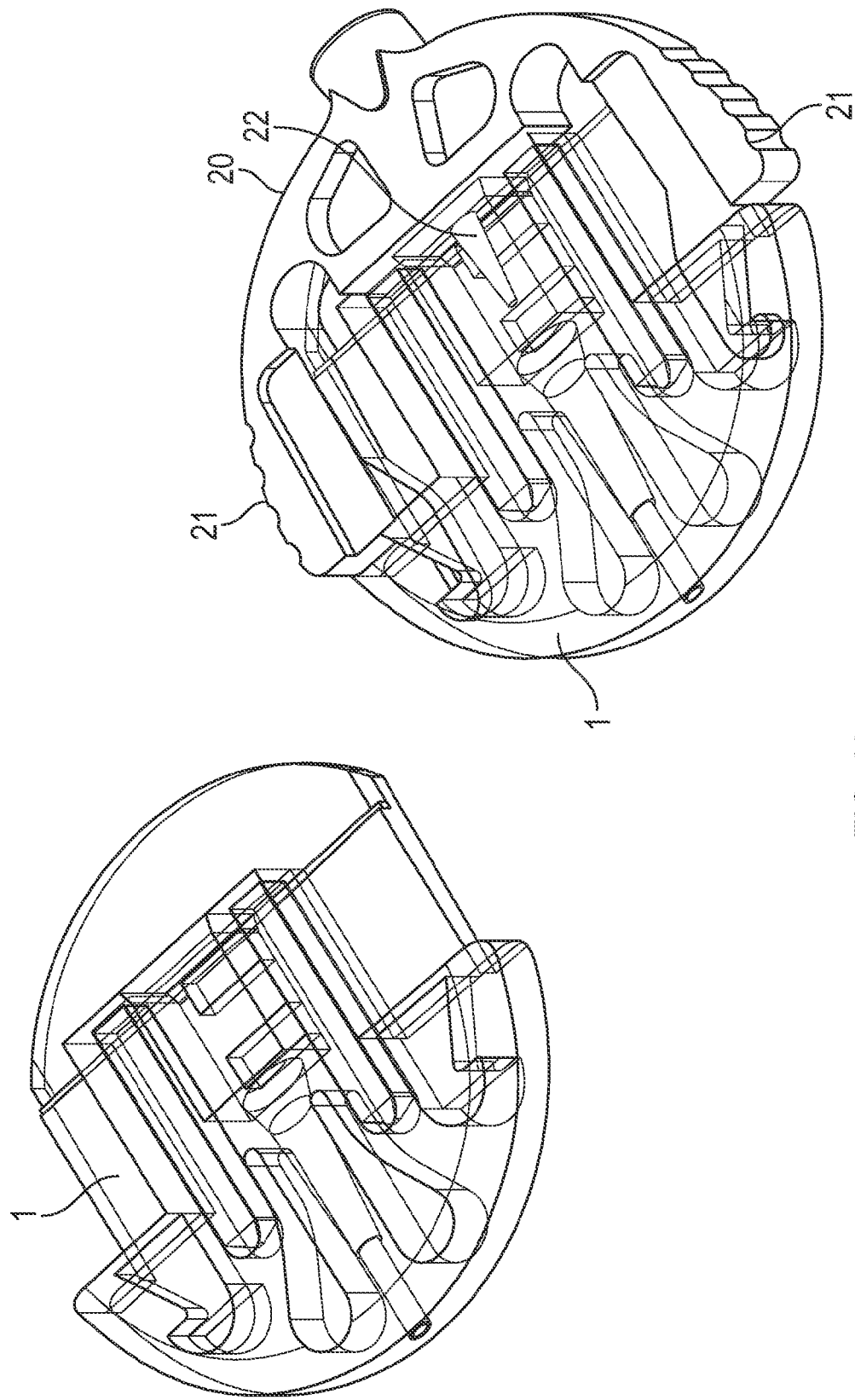
FIG. 10 shows an infusions set comprising an infusion set and a connector.

FIG. 10 shows an infusions set comprising an infusion part 1 and a connector part 20. The connector part 20 is provided with two arms 21 placed on opposite sides of the connector part 20. After insertion of the infusion part 1, which insertion can be made manually or with an inserter, the connector part 20 can form a fluid connection between e.g. an insulin pump and the infusion part 1. In this embodiment the connector part 20 is symmetrical around the plane formed by the two arms 21. This connector part 21 also comprises a connector needle 22 which needle 22 penetrates a barrier layer protecting the inlet to the infusion part 1.

The connector part 20 can be connected to a luer coupling member through a not shown tube. Through the luer coupling it is possible to administer a suitable therapeutical substance, such as insulin from a pump. The connector part can also be a sort of closing part with a suitable entrance for an inserting needle of a syringe. Such a closing part can stay in position for up till three days while the user can have medication, e.g. insulin injected through the entrance in order to reduce trauma to the skin caused by repeated penetration of the skin.

TABLE 1

| | Description of referenced part |
|---|---|
| 1 | Infusion part |
| 2 | Mounting pad |
| 3 | Needle hub |
| 4 | Needle protector |
| 5 | Release paper |
| 6 | Cannula |
| 7 | Insertion needle |
| 8 | Housing contact surface of needle protector |
| 8a | Protruding parts on housing |
| 9 | Infusion part contact surface of needle protector |
| 10 | Protective surface of needle protector |
| 11 | Sled |
| 12 | Guiding means for sled - guides sled relative to housing |
| 12a | Rail corresponding to guiding means 12 for sled |
| 13 | Primary fastening means - fastens spring to sled |
| 14 | Handle |
| 15 | Spring functioning part |
| 16 | Secondary fastening means - fastens spring to housing |
| 17 | Hooks for secondary fastening means |
| 18 | Back stop for secondary fastening means |
| 19 | Spring unit |
| 20 | Connector part |
| 21 | Arms of needle hub 3 and connector part 20 |
| 22 | Connector needle |
| 23 | Means for connecting of infusion part 1 - openings |
| 24 | Means for connecting of connector part 20/needle hub 3 - protruding parts with hooks |
| 25 | Guiding means - connector part 20 |
| 26 | Housing of inserter - stationary part |
| 27 | Upward bend parts of housing |
| 28 | Pressure points |
| 29 | Cover |

The invention claimed is:

1. An inserter comprising:
   a housing;
   a sled unit comprising a handle, the sled unit positioned at least partially within the housing and movable relative to the housing from at least a first position to at least one second position;
   a spring unit, the spring unit operably connecting the housing and the sled unit;
   an infusion part comprising a cannula having an insertion needle extending through the cannula, the infusion part releasably connected to the sled unit; and
   a needle protector releasably connected to the infusion part by a mounting pad connected to a surface of the needle protector and secured to the infusion part, the needle protector comprising a housing contact surface to be used as an axle about which the needle protector is tipped from a first protector position to a second protector position;
   wherein the needle protector is configured to move by pulling the handle backward relative to the housing so that the housing contact surface of the needle protector touches protruding parts of the housing and a front end of the needle protector is elevated.

2. The inserter according to claim 1, wherein the needle protector is releasably connected to the mounting pad.

3. The inserter according to claim 1, wherein the needle protector operably connects to a part of the housing.

4. The inserter according to claim 3, wherein the needle protector comprises a dimensionally stable material fastened to the infusion part in at least two positions.

5. The inserter according to claim 4, wherein the housing contact surface of the needle protector operably contacts the housing and the housing is configured to stop the backward movement of the housing contact surface, and an infusion part contact surface of the needle protector is configured to continually move in the direction of the at least one second position of the sled unit when the sled unit moves from the first position to the at least one second position.

6. The inserter of claim 1, wherein an infusion part contact surface of the needle protector is directly secured to the infusion part.

7. An inserter comprising:
a housing;
a carrier comprising a handle, the carrier positioned at least partially within the housing and movable relative to the housing from at least a first position to at least one second position along a longitudinal axis;
a spring unit, the spring unit operably connecting the housing and the carrier;
an infusion part releasably connected to the carrier, the infusion part comprising a cannula, the cannula having an insertion needle extending therethrough; and
a needle protector releasably connected to the infusion part and comprising a needle covering portion, the needle protector being movably positionable by pulling backward on the handle so that the needle covering portion protects the needle in a first position and a front end of the needle covering portion is generally axially movable to a second position away from the longitudinal axis to expose a distal end of the needle.

8. The inserter of claim 7, wherein an infusion part contact surface of the needle protector is directly secured to the infusion part.

* * * * *